United States Patent [19]

Fisch et al.

[11] Patent Number: 5,208,283
[45] Date of Patent: May 4, 1993

[54] MIXED S-ALKYLTHIOPROPIONIC ACID ESTERS AND POLYMERS STABILIZED THEREWITH

[75] Inventors: Michael H. Fisch, Wayne; Richard D. Peveler, Woodcliff, both of N.J.

[73] Assignee: Witco Corporation, New York, N.Y.

[21] Appl. No.: 770,992

[22] Filed: Oct. 1, 1991

Related U.S. Application Data

[63] Continuation of Ser. No. 467,898, Jan. 22, 1990, Pat. No. 5,057,567.

[51] Int. Cl.$^5$ ............... C07C 323/52; C08K 5/36
[52] U.S. Cl. ..................... 524/302; 560/152
[58] Field of Search ............. 524/302; 560/152

[56] References Cited

U.S. PATENT DOCUMENTS

| | | | |
|---|---|---|---|
| 2,601,063 | 6/1952 | Smith et al. | 560/152 |
| 3,629,194 | 12/1971 | Onishi et al. | |
| 3,637,809 | 1/1972 | Kleiner | 524/289 |
| 3,758,549 | 9/1973 | Dexter et al. | 560/152 |
| 4,080,364 | 3/1978 | Kauder et al. | |
| 4,226,991 | 10/1980 | Nakahara et al. | |
| 4,349,468 | 9/1982 | Nakahara et al. | 524/302 |
| 4,774,355 | 9/1988 | Omori et al. | 560/152 |
| 4,794,138 | 12/1988 | Dunski et al. | |
| 5,055,606 | 10/1991 | Fisch et al. | 560/152 |
| 5,057,567 | 10/1991 | Fisch et al. | 24/302 |
| 5,057,622 | 10/1991 | Chisolm et al. | 560/152 |

OTHER PUBLICATIONS

Smith et al "Addition of Thioghycollic Acid to Alpha-Alkenes" *Acta Chemica Scandinavica* 8, vol. 8, No. 7, 1954.

"Reactions of Mercaptans with Acrylic and Methacrylic Derivatives", Hurd et al, *Journal of American Cemical Society*, vol. 60, pp. 2328-2335, Oct. 1947.

"Methyl 3-n-Dodecylmercaptopropionate", *Journal of American Chemical Society*, vol. 73, p. 4050, 1951.

*Primary Examiner*—Veronica P. Hoke
*Attorney, Agent, or Firm*—Lockwood, Alex, Fitzgibbon & Cummings

[57] ABSTRACT

Mixed esters of pentaerythritol and the like with at least two different 3-alkylthiopropionic acids are provided. Each acid from which the ester is prepared has a different alkyl group. This facilitates tailoring the mixed ester for use as a stabilizer which is especially compatible with a particular polymer resin material. Preferably, each 3-alkylthiopropionic acid is prepared by a direct addition reaction between an alkylmercaptan and acrylic acid or an alkali metal salt thereof, the reaction being carried out by heating the reactants in the presence of an aqueous alkaline solution.

24 Claims, No Drawings

MIXED S-ALKYLTHIOPROPIONIC ACID ESTERS AND POLYMERS STABILIZED THEREWITH

This application is a continuation of copending application Ser. No. 467,898, filed Jan. 22, 1990, now U.S. Pat. No. 5,057,567.

DESCRIPTION

BACKGROUND AND SUMMARY OF THE INVENTION

The present invention generally relates to S-alkylthiopropionic acids which are esterified with pentaerythritol or the like, as well as to methods for making same. More particularly, the invention relates to so-called mixed esters. The mixed esters contain multiple 3-alkylthiopropionic acid groups, at least two of the alkyl chains thereof being of different carbon chain lengths. These mixed esters are useful as stabilizers of organic materials such as polymer resins and the like, and the mixed esters can be tailored to provide properties that are especially suitable for specific stabilizer needs.

Alkyl esters derived from alkylthioalkanoic acids and the like are, in general, known to be useful as stabilizers of organic materials such as polymer resins and the like which are otherwise subject to thermal and oxidative deterioration during processing, extrusion or molding, as well as during use. Esters having this general utility have been proposed and/or prepared in the past. Examples include Dexter et al U.S. Pat. No. 3,758,549, which teaches transesterification procedures for preparation of these general types of products. Included is pentaerythritol tetrakis (3-n-dodecylthiopropionate) formed by a transesterification procedure between methyl 3-n-dodecylthiopropionate and pentaerythritol. Formation of a mixed ester is not suggested.

Prior approaches such as those suggested in Kauder et al U.S. Pat. No. 4,080,364 and Nakahara et al U.S. Pat. No. 4,349,468 teach the preparation of stabilizers for polyolefins by reacting an alpha-olefin with a mercaptocarboxylic acid or an ester of a mercaptocarboxylic acid. Pentaerythritol esters thereof are also described. It is mentioned that the alpha-olefins can take the form of a mixture of alpha-olefins. Typically alpha-olefin reaction schemes such as these produce unwanted isomer byproducts that, if not removed in a separate purification step, lower the quality of the pentaerythritol ester product which is produced. Alkylthiopropionic acids prepared by approaches such as these do not typically directly produce, without special purification, an alkylthiopropionic acid which exhibits a high purity characteristic which will, when reacted with pentaerythritol or the like, form an ester composition which contains a minimum of unwanted byproducts.

Even when ester stabilizers are prepared as esters of pentaerythritol or the like that have exceptional purity, the compatibility thereof with the polymers to be stabilized therewith can be limited. While, for example, the 3-dodecylthiopropionic tetraester of pentaerythritol is solid at room temperature, whereas the 3-octylthiopropionic tetraester of pentaerythritol is liquid at room temperature, compatibility of such esters with a polymer to be stabilized is not readily predictable from this or any other physical property. Compatibility is a useful property usually defined in terms of manifestations of incompatibility which develop during blending of the stabilizer with the polymer, during storage, and/or during extrusion or other formation procedures to which the stabilized polymer is subjected, and can only be determined by experiment. A stabilizer that is especially compatible with a particular polymer or polymer blend will exhibit the absence or at least minimization of any manifestation of incompatibility such as exudation of a liquid or crystallization of a solid additive on the polymer surface. A valuable consequence is that a more compatible stabilizer can be used in greater concentrations, thus resulting in enhanced stabilizing effectiveness.

Variations in physical properties of the alkylthiopropionate tetraesters of pentaerythritol can be achieved by forming esters having alkyl groups of intermediate carbon chain lengths. For example, the 3-decylthiopropionate tetraester with pentaerythritol will tend to have properties generally midway between the dodecyl and octyl tetraesters, and the decyl ester would typically be less volatile than esters prepared from the octyl mercaptan, while being less waxy than esters prepared from the dodecyl mercaptan. However, because each ester molecule has alkyl mercaptan groups of the same carbon chain length, the tailorability of these stabilizers for achieving desired physical and compatibility properties for a specific polymer or polymer blend is limited. These properties can be varied on a somewhat gross scale, but it is not possible to more precisely vary or fine tune the compatibility properties of these types of stabilizers.

Accordingly, it would be desirable to provide stabilizing mixed alkylthiopropionic acid esters of pentaerythritol or the like which incorporate in the same molecule alkyl mercaptan groups which have at least two different alkyl carbon chain lengths. It is further desirable that these mixed esters be prepared in a manner such that the structure of the mixed ester thus produced can be controlled and can be reproduced on a substantially consistent basis. Achieving this objective includes the need to avoid the formation of any undesirable byproducts so that the mixed ester is still a high purity stabilizer product that can be reliably produced as one which provides desired compatibility properties.

By the present invention, stabilizers for extrudable thermoplastic polymers and polymer resin blends are prepared. The stabilizers are mixed esters which are tailored to exhibit specific selected properties for providing excellent compatibility with the polymer resin or polymer resin composition. Each mixed ester has at least two different alkyl groups provided by the alkyl mercaptan from which the mixed ester stabilizer is prepared. In preparing these stabilizers, preferably a 3-alkylthiopropionic acid having an alkyl group of one carbon chain length is prepared by directly reacting the desired alkyl mercaptan with an alkali metal acrylate, the reaction being carried out in the presence of strong base catalyst, followed by acidification and collection. A different 3-alkylthiopropionic acid is prepared in the same manner by using a different alkyl mercaptan having a different alkyl carbon chain length. Additional, different 3-alkylthiopropionic acids can likewise be prepared. The thus prepared different 3-alkylthiopropionic acids are reacted with pentaerythritol or the like, thereby forming the mixed ester stabilizer. When desired, the mixed ester product can be solvent refined.

It is accordingly a general object of the present invention to provide alkylthiopropionate mixed esters and an improved process for preparing same.

Another object of this invention is to provide an improved process for preparation of an improved mixed ester from at least two different S-alkylthiopropionic acids which are prepared by a direct addition reaction mechanism, as well as the mixed ester produced thereby.

Another object of the present invention is to provide improved alkyl mercaptan mixed ester stabilizers which are tailorable to achieve enhanced compatibility with any one of a wide variety of extrudable thermoplastic polymer resins or polymer resin compositions.

Another object of this invention is to provide an improved process for preparing mixed ester stabilizers which includes an improved work-up purification procedure.

Another object of the present invention is to provide a process and product produced thereby wherein a mixed ester stabilizer is prepared from a plurality of 3-alkylthiopropionic acids which are formed without requiring a substantially high excess of acid reagent, thereby minimizing the cost and inefficiency of having to remove excess acid therefrom so as to minimize or eliminate purification at an intermediate stage in the preparation of the mixed ester stabilizer.

These and other objects, features and advantages of the present invention will be clearly understood through a consideration of the following detailed description.

DESCRIPTION OF THE PARTICULAR EMBODIMENTS

The esters prepared according to the present invention are esters of 3-alkylthiopropionic acids with pentaerythritol or the like wherein the esters contain at least two different alkylthiopropionic acid groups in the molecule. These so-called mixed esters are formed by charging at least two different 3-alkylthiopropionic acids into a reaction vessel with pentaerythritol or the like. The two or more acids are selected and are charged at a predetermined ratio in order to form the desired mixed ester(s) having properties that are tailored to fulfill the needs of a stabilizer for a particular polymer resin or polymer resin blend or the like. The mole ratio of the charge can be varied between, for example, about 5:1 and about 1:5 in order to provide an additional measure of tailorability to the extent that the mixed esters will exhibit an increase in the proportion of one particular alkyl group as the ratio of the S-alkylthiopropionic acid having that particular alkyl group is increased in the reaction charge.

A typical mixed ester according to this invention will have the following structure when same is a pentaerythritol ester which is fully esterified to the tetraester structure according to Formula (I) below:

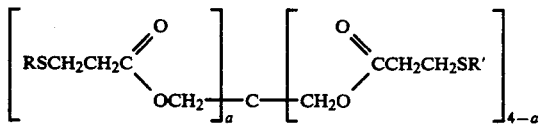

wherein R is an alkyl group having a carbon chain length of between about 4 and about 20 carbon atoms, wherein R' is an alkyl group different from R and which also has a carbon chain length of between about 4 and about 20 carbon atoms, and wherein a is 1, 2 or 3. As discussed in more detail hereinafter, mixed esters having similar alkyl groups (R" and R"') which are each different from R and R' are also possible. Other mixed ester structures may be formed as well. For example, a mixed triester with pentaerythritol would exhibit the structure according to Formula (II) below:

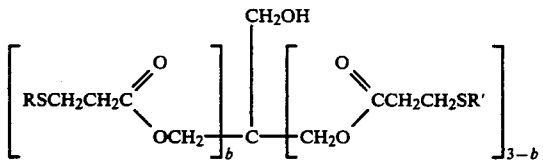

wherein R and R' are as previously defined, and wherein b is 1 or 2.

It will be appreciated that, when a is 0 or 4 a symmetrical tetraester (and not a mixed tetraester) is formed, and when b is 0 or 3 a symmetrical triester (and not a mixed triester) is formed. It will further be appreciated that formation of the mixed esters is statistically favored. In fact, when the procedures according to the invention are followed, mixed esters of the type wherein a is 1, 2 and 3 are the primary esters which are formed. Variations in reactant charges, for example, can be useful in effecting small changes in the properties of the mixed ester reaction product.

Preferably, the 3-alkylthiopropionic acids are each formed from a mercaptan having the desired alkyl group R, R', R" or R"'. With more particular reference to these mercaptans, they will have the formula RSH, R'SH, R"SH or R"'SH, wherein R, R', R" or R"' each has a different carbon chain length of between about 4 and about 20 carbon atoms. Exemplary mercaptans in this regard include n-butyl mercaptan, n-octyl mercaptan, n-decyl mercaptan, n-dodecyl mercaptan and the like. In accordance with the preferred aspects of this invention, each 3-alkylthiopropionic acid is prepared by a direct addition reaction procedure whereby each selected mercaptan undergoes an addition reaction with an acid reactant or salt thereof to add the propionic acid component of the 3-alkylthiopropionic acid to the mercaptan.

Concerning the acid reactant or salt which reacts with the mercaptan, same may be characterized as an acid reactant which is charged to the reaction vessel as acrylic acid or as a derivative, typically an alkali metal salt thereof. Generally, equimolar charges of each selected mercaptan and of the acid reactant are utilized, although the acid component may be present at a concentration slightly in excess of the equimolar level. This addition reaction is run under strongly basic conditions, and the acid reactant is perhaps more properly characterized as an alkali metal acrylate, with the alkali metal being that of the base component which catalyzes the addition reaction. A 3-alkylthiopropionic acid thus prepared will have the formula $RSCH_2CH_2COOH$, wherein R is as previously defined herein. Two or more of these acids are utilized in accordance with the present invention, with each acid having a different alkyl group, which may be designated as R, R', R" or R"' as defined herein.

In preparing the two or more 3-alkylthiopropionic acids, any strong base can be utilized as the catalyst, provided an aqueous solution thereof will impart a pH of at least about 11 to the reaction composition. The strength of the base can be generally defined as one wherein a 1% aqueous solution thereof has a pH of at least about 13. Typical strong bases in this regard include aqueous potassium hydroxide, aqueous sodium hydroxide and the like. When this procedure is followed, it is important that the reaction composition incorporate an adequate concentration of this strong base. The amount is to be adequate to convert any charged acrylic acid to its alkali salt, while still providing enough strong base to act as a catalyst for the addition reaction. For example, the reaction composition should typically include at least about 1.05 mole of strong base per mole of acrylic acid charged into the reaction vessel.

When this base catalyzed addition reaction is followed, it is carried out with a sufficient quantity of solvent within the reaction composition. Preferably, the solvent is a mixture of organic solvent and water. Water alone may be suitable for acids made from mercaptans with short chain lengths such as those having four carbon atoms, but using the solvent mixture is believed to be important in most cases. For example, the reaction is faster and less subject to foaming when the solvent is water combined with an organic solvent. Preferred organic solvents in this regard are oxygenated organic solvents, typically ones that are water-soluble oxygenated compounds exhibiting a ratio of from one to four carbon atoms for every oxygen atom. Exemplary solvents in this regard include 2-propanol, tert-butyl alcohol, tetrahydrofuran, ethanol, methanol, 2-ethoxyethanol, and the like. An especially preferred solvent is a mixture of water and 2-propanol (isopropyl alcohol). A typical ratio of water to oxygenated organic solvent is between about 9 to 1 and about 1 to 9.

In a preferred aspect of this process, the mercaptan is added to the reactant composition after it already contains the alkali metal acrylate. It has been determined that, even when the reaction is carried out in the presence of oxygen, the incidence of undesirable disulfide formation is reduced significantly with this order of addition of reactants, when compared with the reverse order of addition, which can be characterized as the addition of acrylic acid to the reaction composition which already contains sodium mercaptide. When the reverse order of addition is desired, typically adequate control of disulfide formation can be attained by blanketing the reaction mixture with nitrogen, when this is feasible.

After the addition reaction has progressed to the desired extent, the 3-alkylthiopropionic acid is isolated from the reaction composition by proceeding first with acidification of the reaction mixture, typically with a suitable aqueous mineral acid. Aqueous and organic layers thereby defined are then separated. If necessary, depending upon the carbon chain length of the mercaptan reactant, the layers are maintained at a temperature high enough to keep the alkylthiopropionic acid molten. After separation has been completed, the collected organic phase is preferably vacuum stripped in order to remove and recover the organic solvent and thereby provide the 3-alkylthiopropionic acid addition reaction product.

Once formed, the two or more 3-alkylthiopropionic acids are esterified with the desired polyhydroxyl component, typically pentaerythritol. Usually this esterification to form the mixed ester product is carried out at an elevated temperature and under acid catalysis. Typically suitable catalysts in this regard are para-toluenesulfonic acid, xylenesulfonic acid, methanesulfonic acid, ethanesulfonic acid, and the like.

It is especially preferred that this esterification procedure be followed by a work-up operation wherein excess acid is removed by solvent refining the organic phase with an organic solvent. The solvent refining medium is a single organic solvent or a blend of at least two organic solvents, depending upon the specific alkylthiopropionic mixed ester being prepared. Exemplary components of this type include low molecular weight alcohols and low molecular weight esters, including materials such as methanol, ethanol, isopropyl alcohol, ethyl acetate, isopropyl acetate, and the like. It has been found that a suitable solvent will improve work-up purification procedures, when desired, in a manner that minimizes the expense thereof. Typically preferred solvents include methanol and methanol blended with isopropyl alcohol. An exemplary blend is a 4:1 mixture of methanol and isopropyl alcohol. A typical two-component solvent blend would be at a ratio of between about 9 to 1 and about 1 to 9.

When greater than two different 3-alkylthiopropionic acids are used to prepare the esters according to the present invention, esters of pentaerythritol and the like would include three or more different alkylmercaptan chains. When three different alkylthiopropionic acids are used, the ester would exhibit the following structure:

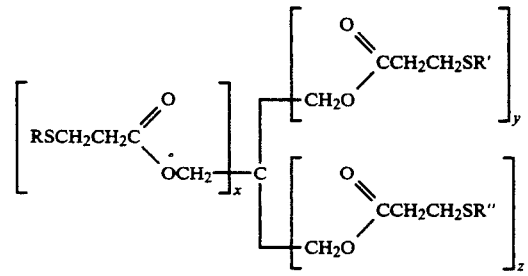

wherein R and R' are as previously defined herein, wherein R" is an alkyl group different from R and R' and which also has a carbon chain length of between about 4 and about 20, and wherein each of x, y and z are 1 or 2 such that x plus y plus z totals 4. When four different 3-alkylthiopropionic acids are used, the ester will have the following structure:

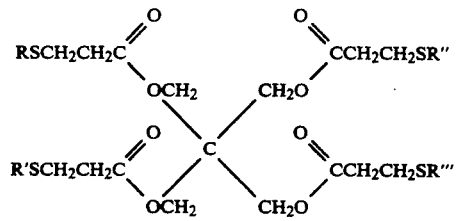

wherein R, R' and R" are as defined herein, and wherein R'" is another alkyl group having a carbon chain length between about 4 and about 20, which alkyl group is different from that of each of the alkyl groups of the other three alkylthiopropionic acids.

Esters of the type discussed herein are typically suitable for use as stabilizers for extrudable thermoplastic polymers, polymer resins and polymer compositions or blends. Included are various crystalline or rubbery olefin polymers prepared from olefin monomers including ethylene, propylene, 1-butene, 1-hexene, 1-decene, and 4-methyl-1-pentene used singly or in combination; copolymers of ethylene with oxygenated carboxylic acid or ester monomers illustrated by ethyl acrylate, vinyl acetate, and methacrylic acid; styrene polymers including styrene homopolymer and styrene polymer systems incorporating additional monomers such as butadiene, isoprene, acrylonitrile, methyl methacrylate, maleic anhydride, or maleate esters; extrudable thermoplastic polyesters including polycarbonates, polyarylates, glycol terephthalates and proprietary polymers and polymer blends having a terephthalate ester component and a rubbery type of component.

Various mixed ester stabilizers prepared according to this invention have different physical properties, thereby enabling exceptionally precise tailoring of the stabilizer to best suit the particular polymer material being stabilized. This provides the advantage of improved compatibility with the particular polymer material leading to the substantial absence of any manifestations of incompatibility such as exudation of a liquid or crystallization of a solid additive on the polymer surface. For example some mixed ester stabilizers take on the consistency of a wax at room temperature and start to melt above room temperature. Others may be solid masses at room temperature which do not begin to melt until above room temperature, such as 32° C. Others can be liquid at room temperature. Also, a wide variety of melting profiles can be tailored as desired.

Advantageous use levels of the ester stabilizers of this invention in extrudable thermoplastic polymers range from about 0.01 to about 5% by weight of the polymer, preferably from about 0.2% to about 2% by weight.

The following examples illustrate the preparation of mixed esters according to the present invention.

EXAMPLE 1

To a stirred solution of 0.50 mole of 1-dodecylmercaptan in isopropanol under a nitrogen atmosphere at 25° C., 0.58 mole of 50% sodium hydroxide aqueous solution was added in one portion. The mixture exothermed to 70° C., and a white precipitate formed. Isopropyl alcohol was added to the slurry, which was cooled to 32° C. with a water bath. Next, 0.525 mole of acrylic acid was added dropwise over a 15 minute period. Additional isopropyl alcohol (in two aliquots) was added, the exothermal reaction proceeded at 40° C., and after 20 minutes of stirring, additional water was added. The solid components slowly dissolved in order to provide a homogeneous solution, which was refluxed for two hours. After standing overnight at 25° C., the sample was analyzed to have 0.03% dodecylmercaptan.

Acidification was carried out by heating the reaction composition to 45° C. and adding 50% aqueous sulfuric acid, after which same was poured into a separatory funnel, and the aqueous layer was drained. Washing was next carried out with three portions of water, with the third wash including a small amount of sodium sulfate. The washed organic layer was then vacuum stripped with a Roto-Vap rotary evaporator to give 3-dodecylthiopropionic acid product having a melting point of 59°–62° C. The yield by GLC was 99.0% having an acid value of 204.2 (theory 204.4).

A charge of 1.00 mole of n-octylmercaptan in an isopropyl alcohol and water 1:1 blend was added to a vessel. At room temperature, 1.16 mole of sodium hydroxide in an equal volume of water was added to the vessel, and an exotherm proceeded at 50° to 60° C. Over a 30-minute period, 1.05 mole of acrylic acid was added dropwise, the temperature was then raised to 85° C., and the mixture was allowed to reflux for 2 hours. After cooling to 55° C., 70% aqueous sulfuric acid (0.59 mole) was added, with stirring for 30 minutes, followed by pouring into a separatory device. The aqueous layer was drained off, and the organic layer was washed with an equal volume of water containing 2% sodium sulfate. After vacuum stripping at 60° C., the reaction product was analyzed to contain 0.04% octylmercaptan and a yield of 98.6% of 3-octylthiopropionic acid product.

Slightly in excess of two moles of 3-dodecylthiopropionic acid, slightly in excess of two moles of 3-octylthiopropionic acid, one mole of pentaerythritol, and 20 grams (0.105 mole) of para-toluenesulfonic acid monohydrate catalyst were added to a reaction vessel. A vacuum of approximately 25 mmHg was applied, and the temperature was raised to 135° C. and held there for 7 hours, with stirring. In the work-up, the excess acid was removed by repeated hot washes of a 4:1 blend of methanol and isopropyl alcohol until the acid value of the product was below 1. The product was thoroughly vacuum stripped at 90° C. and filtered hot. The product was a white wax at room temperature, and starts to melt above 25° C. The reaction product was analyzed to contain 0.022% mercaptan and a yield of 91.2% of mixed ester product at an acid value of 0.255. IR analysis (neat) showed peaks at 1744, 1466, 1238 and 1140 cm$^{-1}$.

The product is a mixture of mixed esters. Liquid chromatography shows many peaks. A product following a statistical distribution of esters that could be prepared from the reactants according to this Example could show nine peaks including the two symmetrical tetraesters not in accordance with the present invention and which can be described by Formula I hereinabove when a is 0 and 4. Three mixed esters according to the present invention are defined by Formula I when a is 1, 2 and 3. Triesters are also statistically possible, including two symmetrical triesters, which can be represented by Formula II hereinabove wherein b is 0 and 3. Two statistically possible mixed triesters are defined when b is 1 and 2.

Liquid chromatography analysis of the reaction product does show that the reaction product is different from a simple blend of the two statistically possible symmetrical tetraesters. This is readily determined because the symmetrical tetraesters have known, characteristic retention times alone or blended with each other or as components of the reaction product. Retention times of the symmetrical triesters are also known. Confirmation of the inclusion of the mixed esters within the reaction product is achieved (and peaks can be at least tentatively assigned) for the mixed esters of the invention by observing which peaks are increased by the use of increased proportions of one of the alkylthiopropionic acids charged to the reaction vessel.

EXAMPLE 2

The procedure of Example 1 was followed, except in this Example, slightly in excess of six moles of the 3-dodecylthiopropionic acid were charged to the reaction vessel, all other reactants and quantities thereof and process conditions remaining the same as Example 1. The product was a white solid mass at room temperature which melts above 32° C. The reaction product was analyzed to contain 0.025% mercaptan and a yield of 91% of reaction product. The IR spectra peaks (neat)

were at 1733, 1467, 1239 and 1138 cm$^{-1}$ The acid value was 0.31.

EXAMPLE 3

The procedure of Example 1 was followed, except in this Example, slightly in excess of six moles of the 3-octylthiopropionic acid were charged to the reaction vessel, all other reactants and quantities thereof and process conditions remaining the same as Example 1. The reaction product was a clear colorless liquid at room temperature having an $n_D^{25}$ of 1.4890 and an acid value of 0.856. The percentage of mercaptan in the reaction product was 0.004%, and the yield was 90.1%. The specific gravity was 0.98. The IR spectra peaks (neat) were at 1744, 1466, 1238 and 1140 cm$^{-1}$

EXAMPLE 4

A 3-liter, 4-necked round bottom flask was charged with 530.8 grams (3.008 moles) of 98.8% n-decylmercaptan, 600 ml. of isopropyl alcohol and 600 ml. of water. The flask was equipped with a heating mantle, a thermometer, a reflux condenser, an additional funnel and a mechanical stirrer. Nitrogen (900 ml./min.) was introduced through the top of the condenser by way of a Firestone valve. 140.6 grams (3.459 moles) of 98.4% sodium hydroxide in a 50% aqueous solution were added to the stirred mixture over one hour. The temperature rose to 38° C., and 227.6 grams (3.158 moles) of acrylic acid were then added over 55 minutes, raising the temperature to 62° C. The mixture was refluxed at 86° C. for four hours, and the nitrogen flow rate of 900 ml./min. continued overnight. The mercaptan value at this time was analyzed at less than 0.02%.

Next, 190.9 grams (1.907 moles) of 98% sulfuric acid was dissolved in a 50% aqueous solution and added to the stirred mixture at 60° C. Stirring continued for 15 minutes, after which the layers were permitted to separate. The lower layer had a pH of 3. The mixture was transferred to a separatory funnel where the lower layer was removed. The product was then washed with two aliquots of 500 ml. of hot (approximately 60° C.) sodium sulfate solution at a concentration of about 2 to 3%. The washed product was stripped with a rotary evaporator. The yield was 734.0 grams, or 99.0%. The acid value analyzed at 227.0. According to gas chromatography analysis, the product was at least 97.4% pure, with only 0.2% isopropyl acetate ester.

A mixed ester product of Bis-(3-n-dodecylthiopropionoxy) Bis-(3-n-decylthiopropionoxy) neopentane was prepared. 134.7 grams (0.547 mole) of the 3-n-decylthiopropionic acid prepared as specified herein was mixed with 150.0 grams (0.547 mole) of 3-n-dodecylthiopropionic acid within a 1-liter, 4-necked round bottom flask, with agitation by a mechanical stirrer. Next, 35.0 grams (0.26 mole) of pentaerythritol were added, followed by 3.9 grams (0.021 mole) of para-toluenesulfonic acid catalyst. The flask was also equipped with a thermometer, a heating mantle, a vacuum take-off adaptor and a pressure relief valve. Vacuum was applied immediately, and while the temperature rose to 110° C., the pressure was carefully lowered to 38 torr, during which water was driven off. Thereafter, the temperature was raised to 135° C., and the mixture was heated for five hours during which time the pressure dropped to 25 torr.

An acid value analysis indicated 10.9. The product was washed with 500 ml. of hot 2 to 3% sodium sulfate, followed by stripping with a rotary evaporator, after which the product was washed with four 300 ml. aliquots of hot methanol, the acid value thereafter being 1.1. An acid value of 0.3 was achieved after washing with three additional 300 ml. aliquots of hot methanol. The product was stripped again to remove methanol, and the yield was 258.4 grams (89.9%) of a product having a melting point of 36°–38° C.

Liquid chromatography testing showed a distribution of tetraester products, including a substantial percentage of mixed tetraester products, within the product yield. The analyzed product distribution correlated well with the expected theoretical product distribution. These data can be summarized as follows:

| Formula (I) Tetraester | Theoretical Percentage | LC Analysis Percentage |
|---|---|---|
| a = 4 | 6.25 | 5.9 |
| a = 3 | 25.00 | 24.9 |
| a = 2 | 37.50 | 37.0 |
| a = 1 | 25.00 | 26.0 |
| a = 0 | 6.25 | 6.2 |

The Formula (I) tetraester reported upon is one wherein R has a carbon chain length of 10 and is from the decyl mercaptan, while R' has a carbon chain length of 12 and is from the dodecyl mercaptan, and wherein "a" in Formula I is as indicated hereinabove.

EXAMPLE 5

A Bis-(3-n-decylthiopropionoxy) Bis-(3-n-octylthiopropionoxy) neopentane was prepared. 150 grams (0.609 mol) of 3-n-decylthiopropionic acid and 132.9 grams (0.609 mol) of 3-n-octylthiopropionic acid were mixed, rendered molten and stirred within a reaction vessel, to which 39.5 grams (0.290 mol) of pentaerythritol were added, followed by 4.4 grams (0.023 mol) of para-toluenesulfonic acid catalyst. A vacuum of 40 torr was applied, and the mixture was heated to 135° C. Heating was continued for five hours, after which a liquid product having an acid value of 11.4 was obtained. This product was washed with 500 ml. of hot 3% sodium sulfate and then vacuum stripped It was washed with six 300 ml. aliquots of hot methanol, after which the acid value was 0.4. The yield was 250.9 grams, or 87.1 percent. A comparison of the actual product distribution versus the statistical distribution can be summarized as follows:

| Formula (I) Tetraester | Theoretical Percentage | LC Analysis Percentage |
|---|---|---|
| a = 4 | 6.25 | 5.5 |
| a = 3 | 25.00 | 24.2 |
| a = 2 | 37.50 | 37.8 |
| a = 1 | 25.00 | 25.4 |
| a = 0 | 6.25 | 7.1 |

In this Formula (I) product, R had a carbon chain length of 8, R' had a carbon chain length of 10, and "a" is as indicated.

It will be understood that the embodiments of the present invention which have been described are illustrative of some of the applications of the principles of the present invention. Numerous modifications may be made by those skilled in the art without departing from the true spirit and scope of the invention.

We claim:

1. A mixed ester of pentaerythritol with a plurality of 3-alkylthiopropionic acids wherein each alkyl component thereof has from 4 to 12 carbon atoms, the mixed ester having been prepared by the process comprising the steps of:
   (a) providing an alkyl mercaptan of the formula RSH, wherein R is an alkyl group having from 4 to 12 carbon atoms;
   (b) reacting said RSH alkyl mercaptan by a direct addition reaction with an acrylic acid component selected from the group consisting of acrylic acid and an alkali metal acrylate, and recovering a 3-alkylthiopropionic acid having R as its alkyl group, said direct addition reaction being at a pH of at least about 11;
   (c) providing an alkyl mercaptan of the formula R'SH, wherein R' is an alkyl group different from R and having from 4 to 12 carbon atoms;
   (d) reacting said R'SH alkyl mercaptan by a direct addition reaction with an acrylic acid component selected from the group consisting of acrylic acid and an alkali metal acrylate, and recovering a 3-alkylthiopropionic acid having R' as its alkyl group, said direct addition reaction being at a pH of at least about 11;
   (e) reacting together said 3-alkylthiopropionic acid having R as its alkyl group, said 3-alkylthiopropionic acid having R' as its alkyl group, and pentaerythritol in order to form a mixed tetraester product having a molecular structure containing both R and R' groups; and
   (f) selecting, prior to said steps (a) and (c), said R and R' alkyl groups whereby said mixed tetraester product is tailored for maximizing its compatibility with an extrudable polymer resin component blended with said mixed tetraester product into a stabilized polymer composition.

2. The mixed ester according to claim 1, wherein said mixed ester has tetraester components having the formula:

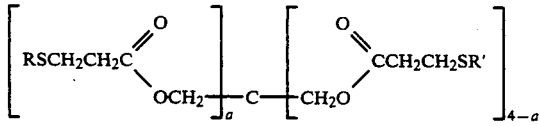

wherein R and R' are as defined in claim 1 and wherein a is 1, 2 or 3.

3. The mixed ester according to claim 1, wherein said reacting step (e) includes charging said 3-alkylthiopropionic acids at a mole ratio between about 5:1 and about 1:5.

4. The mixed ester according to claim 1, wherein said 3-alkylthiopropionic acids are selected from the group consisting of 3-butylthiopropionic acid, 3-octylthiopropionic acid, 3-decylthiopropionic acid and 3-dodecylthiopropionic acid.

5. The mixed ester according to claim 1, wherein said reacting steps (b) and (d) are carried out in an alkaline reaction solution and in the presence of an aqueous alkaline catalyst.

6. The mixed ester according to claim 5, further including acidifying said reaction solution prior to recovery of each said 3-alkylthiopropionic acid.

7. The mixed ester according to claim 5, wherein said reaction solution has a pH of at least about 11.

8. The mixed ester according to claim 5, wherein said alkaline catalyst is a strong base and a 1% aqueous solution thereof has a pH of at least about 13.

9. The mixed ester according to claim 5, wherein said alkaline catalyst is an alkali metal hydroxide.

10. The mixed ester according to claim 5, wherein each said alkyl mercaptan and each said acrylic acid component are at substantially equimolar concentrations, and said alkaline catalyst is an alkali metal hydroxide added at a concentration of at least about 1.05 mole per mole of charged acrylic acid component.

11. The mixed ester according to claim 1, wherein at least about 1.05 mole of an alkaline catalyst is added per mole of acrylic acid component charged during said reacting steps (b) and (d).

12. The mixed ester according to claim 1, further including solvent refining said mixed ester product with an organic solvent.

13. The mixed ester according to claim 12, wherein said organic solvent is a blend of lower aliphatic alcohols.

14. A mixed ester stabilizer component for inclusion within a stabilized polymer composition including the mixed ester stabilizer component and an extrudable polymer resin component, said mixed ester stabilizer component comprising a mixed tetraester of pentaerythritol with a plurality of 3-alkylthiopropionic acid, said mixed tetraester comprising at least one tetraester component having the formula:

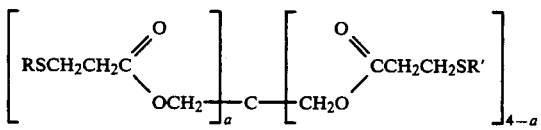

wherein R is an alkyl group having 4 to 12 carbon atoms, wherein R' is an alkyl group different from R and having from 4 to 12 carbon atoms, and wherein a is 1, 2 or 3, and said R and R' alkyl groups are selected whereby said mixed ester stabilizer component exhibits maximized compatibility with the particular extrudable polymer resin component of the stabilized polymer composition.

15. A stabilized polymer composition including an extrudable polymer resin component and a stabilizer component, wherein said stabilizer component comprises a mixed tetraester of pentaerythritol with a plurality of 3-alkylthiopropionic acids, said mixed tetraester including at least one tetraester component having the formula:

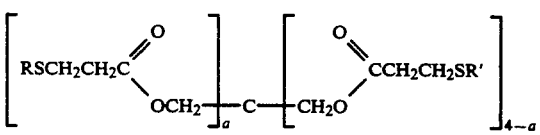

wherein R is an alkyl group, wherein R' is an alkyl group different from R, wherein a is 1, 2 or 3, and wherein said 3-alkylthiopropionic acids are selected from the group consisting of 3-butylthiopropionic acid, 3-octylthiopropionic acid, 3-decylthiopropionic acid and 3-dodecylthiopropionic acid.

16. The mixed ester according to claim 14, wherein said 3-alkylthiopropionic acids are selected from the group consisting of 3-butylthiopropionic acid, 3-octylthiopropionic acid, 3-decylthiopropionic acid and 3-dodecylthiopropionic acid.

17. The mixed ester according to claim 14, wherein R has a carbon chain length of 8 and R' has a carbon chain length of 12.

18. The mixed ester according to claim 14, wherein R has a carbon chain length of 8 and R' has a carbon chain length of 10.

19. The mixed ester according to claim 14, wherein R has a carbon chain length of 10 and R' has a carbon chain length of 12.

20. The stabilized polymer composition according to claim 15, wherein R has a carbon chain length of 8 and R' has a carbon chain length of 12.

21. The stabilized polymer composition according to claim 15, wherein R has a carbon chain length of 8 and R' has a carbon chain length of 10.

22. The stabilized polymer composition according to claim 15, wherein R has a carbon chain length of 10 and R' has a carbon chain length of 12.

23. A stabilized polymer composition comprising an extrudable polymer resin component and a stabilizer component, wherein said stabilizer component comprises a mixed tetraester of pentaerythritol with a plurality of 3-alkylthiopropionic acids each having an alkyl component of from 4 to 12 carbon atoms, said mixed tetraester stabilizer component being of maximized compatibility with the particular extrudable polymer resin component and being prepared by a process including the steps of:

(a) providing an alkyl mercaptan of the formula RSH, wherein R is an alkyl group having from 4 to 12 carbon atoms;

(b) reacting said RSH alkyl mercaptan by a direct addition reaction with an acrylic acid component selected from the group consisting of acrylic acid and an alkali metal acrylate, and recovering a 3-alkylthiopropionic acid having R as its alkyl group, said direct addition reaction being at a pH of at least about 11;

(c) providing an alkyl mercaptan of the formula R'SH, wherein R' is an alkyl group different from R and having from 4 to 12 carbon atoms;

(d) reacting said R'SH alkyl mercaptan by a direct addition reaction with an acrylic acid component selected from the group consisting of acrylic acid and an alkali metal acrylate, and recovering a 3-alkylthiopropionic acid having R' as its alkyl group, said direct addition reaction being at a pH of at least about 11;

(e) reacting together said 3-alkylthiopropionic acid having R as its alkyl group, said 3-alkylthiopropionic acid having R' as its alkyl group, and pentaerythritol in order to form a mixed tetraester product having a molecular structure containing both R and R' groups; and (f) selecting, prior to said steps (a) and (c), said R and R' alkyl groups whereby said mixed tetraester product is tailored for maximizing its compatibility with an extrudable polymer resin component blended with said mixed ester product into a stabilized polymer composition.

24. The stabilized polymer composition according to claim 23, wherein said 3-alkylthiopropionic acids are selected from the group consisting of 3-butylthiopropionic acid, 3-octylthiopropionic acid, 3-decylthiopropionic acid and 3-dodecylthiopropionic acid.

* * * * *

UNITED STATES PATENT AND TRADEMARK OFFICE
CERTIFICATE OF CORRECTION

PATENT NO. : 5,208,283
DATED : May 4, 1993
INVENTOR(S) : Fisch et al

It is certified that error appears in the above-identified patent and that said Letters Patent is hereby corrected as shown below:

TITLE PAGE
Under Inventors: "Woodcliff" should read --Woodcliff Lake--.
Under Other Publications, "Thioghycollic" should read --Thioglycolic-- (1st line); and "Cemical" should read --Chemical-- (6th line).
  Col. 13, line 12, "20." should read --22.--; line 13, "15," should read --20,--; line 15, "21." should read --23.--; line 16, "15," should read --20,--; line 18, "22." should read --24.--; line 19, "15," should read --20,--; line 21, "23." should read --20.--.
  Col. 14, line 30, "24." should read --21.--; line 31, "23," should read --20--.

Signed and Sealed this

Twenty-third Day of August, 1994

Attest:

BRUCE LEHMAN

*Attesting Officer*    *Commissioner of Patents and Trademarks*